US011730372B2

(12) United States Patent
Westerhof et al.

(10) Patent No.: US 11,730,372 B2
(45) Date of Patent: Aug. 22, 2023

(54) ACCESSORY DEVICE AND IMAGING DEVICE

(71) Applicant: KONINKLIJKE PHILIPS N.V., Eindhoven (NL)

(72) Inventors: Willem Auke Westerhof, Drachten (NL); Yue Wu, Amsterdam (NL); Matthijs Platje, Groningen (NL); Pascal Driessen, Drachten (NL); Willem Minkes, Emmeloord (NL); Marco Tenback, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 528 days.

(21) Appl. No.: 16/339,767

(22) PCT Filed: Oct. 17, 2017

(86) PCT No.: PCT/EP2017/076516
§ 371 (c)(1),
(2) Date: Apr. 5, 2019

(87) PCT Pub. No.: WO2018/073266
PCT Pub. Date: Apr. 26, 2018

(65) Prior Publication Data
US 2020/0037882 A1 Feb. 6, 2020

(30) Foreign Application Priority Data
Oct. 18, 2016 (EP) .................................... 16194332

(51) Int. Cl.
*A61B 5/00* (2006.01)
(52) U.S. Cl.
CPC ............ *A61B 5/0077* (2013.01); *A61B 5/441* (2013.01); *A61B 5/6898* (2013.01); *A61B 2576/02* (2013.01)

(58) Field of Classification Search
CPC ....... A61B 5/00; A61B 5/0059; A61B 5/0077; A61B 5/0531; A61B 5/441; A61B 5/442;
(Continued)

(56) References Cited

U.S. PATENT DOCUMENTS 5,530,650 A * 6/1996 Biferno .................. B64D 39/00
244/135 A
2001/0050765 A1* 12/2001 Antonelli ........... G06K 9/00046
356/71

(Continued)

FOREIGN PATENT DOCUMENTS

EP 2759981 A1 7/2014
JP 8182654 A 7/1996
(Continued)

OTHER PUBLICATIONS

"Skin-Glossymeter GL-200", Mar. 13, 2016, MicroCaya (Year: 2016).*

(Continued)

*Primary Examiner* — Patrick Fernandes
*Assistant Examiner* — Anna Roberts

(57) ABSTRACT

The present invention relates to an accessory device (20) for an image-capturing device (10) for capturing a skin image of a subject's skin comprising a tubular member (21) having a first opening (22) at its first end (23) configured to surround a light source (11) and an image sensor (12) included in the image-capturing device (10) and a second opening (24) at its second end (25) configured to surround a skin portion (101) and two mirrors (26, 27) arranged within the tubular number (21) at its second end (25), wherein a first mirror (26) is arranged to retied light (30) emitted by the light source (11) towards the skin portion (101) and a second mirror (27) is arranged to reflect light (31) reflected from the skin portion (101) towards the image sensor (12). The accessory device can be coupled to an image-capturing device to acquire an (Continued)

image of a skin portion, which is evaluated to determine a skin parameter, such as skin gloss.

8 Claims, 5 Drawing Sheets

(58) Field of Classification Search
CPC ..... A61B 5/443; A61B 5/1032; A61B 5/4272; A61B 5/4836; A61B 5/4875; A61B 5/6843; A61B 5/6898; A61B 5/7264; A61B 2576/02
USPC .......................................................... 600/306
See application file for complete search history.

(56) References Cited

U.S. PATENT DOCUMENTS

| | | | |
|---|---|---|---|
| 2003/0026110 A1* | 2/2003 | Satoh | H04N 5/2256 362/572 |
| 2004/0110113 A1* | 6/2004 | Huang | G09B 19/00 434/100 |
| 2004/0257439 A1 | 12/2004 | Shirai | |
| 2005/0271295 A1 | 12/2005 | Tabata | |
| 2006/0210154 A1 | 9/2006 | Leveque | |
| 2007/0040907 A1* | 2/2007 | Kern | A61B 5/0059 348/77 |
| 2008/0214907 A1 | 9/2008 | Gutkowicz-Krusin | |
| 2009/0245603 A1 | 10/2009 | Koruga | |
| 2012/0041282 A1 | 2/2012 | Nichol | |
| 2013/0300919 A1* | 11/2013 | Fletcher | H04N 5/2254 348/360 |
| 2014/0099027 A1 | 4/2014 | Watanabe | |
| 2015/0156298 A1* | 6/2015 | Ikemoto | A61B 5/6898 455/556.1 |
| 2015/0254500 A1 | 9/2015 | Izumi | |
| 2015/0355527 A1 | 12/2015 | Takahashi | |
| 2016/0106198 A1 | 4/2016 | Yoshida | |
| 2016/0120604 A1 | 5/2016 | Horton | |
| 2016/0166150 A1 | 6/2016 | Vilenskii | |
| 2016/0166194 A1 | 6/2016 | Gareau | |
| 2016/0213316 A1 | 7/2016 | Hyde | |

FOREIGN PATENT DOCUMENTS

| | | | |
|---|---|---|---|
| JP | 2013033017 A | * | 2/2013 |
| JP | 2015197617 A | | 11/2015 |
| WO | 2014041585 A1 | | 3/2014 |
| WO | 2015105870 A1 | | 7/2015 |

OTHER PUBLICATIONS

"Skin-Glossymeter GL200-Measuring Gloss on Skin, Lips, and Hair", Courage+Khazaka (Year: 2016).*

CK electronic, "Skin-Glossymeter GL 200", May 8, 2015, retrieved via https://web.archive.org/web/20150508115817/http://www.courage-khazaka.de:80/index.php/en/component/content/article/59-english/products/scientific/134-skin-glossymeter (Year: 2015).*

* cited by examiner

ACCESSORY DEVICE AND IMAGING DEVICE

This application is the U.S. National Phase application under 35 U.S.C. § 371 of International Application No. PCT/EP2017/076516, filed on Oct. 17, 2017, which claims the benefit of International Application No. 16194332.9, filed Oct. 18, 2016. These applications are hereby incorporated by reference herein.

FIELD OF THE INVENTION

The present invention relates to an accessory device for an image-capturing device for capturing a skin image of a subject's skin. Further, the present invention relates to an imaging device and to a method for determining a subject's skin parameter, such as gloss and/or hydration.

BACKGROUND OF THE INVENTION

Skin is the largest organ of a human body. It has multiple properties which are influenced by many factors and it can tell a lot about a person's health. Its appearance is important for how a person is perceived by other people. Mostly (but not only) in Asia many people suffer from "oily skin", where a combination of productive sebum glands together with a warm, moist climate lead to a non-hygienic shiny appearance. Though the issue occurs in both males and females, males mostly have no clue how to deal with their oily skin. They do not know when to cleanse, how frequently to cleanse, with what to cleanse and how to cleanse. One of the typical issues that occur is that men cleanse too often, with too aggressive products, resulting in a very dry skin, stimulating the sebum gland activity even more. If these men would have quantified information on the shiny appearance of their skin, together with data on the hydration level of their skin, this would enable them to choose the optimal skin care routine for their skin. Defining the optimal skin care routine could for instance be executed via a guiding/coaching app that is installed on a person's smartphone, using the data from a gloss and hydration measurement.

Gloss (specular reflection) measurement is a known method to assess a person's skin oiliness, but is only partly related to it. Other physiological properties like skin roughness and facial shape have a substantial effect on gloss, leading to substantial differences in absolute gloss levels between people, without direct relation to oiliness.

Besides that, methods for removing facial oil, like cleansing, can also lead to a smoother skin surface and to more gloss, while still improving the hygienic appearance of that person.

Currently, there are consumer products available for measuring hydration, however devices for measuring skin gloss are mainly for professional use and too expensive for most consumers. Hence, there is a need for efficient and simple solutions enabling measuring the amount of gloss (i.e. the gloss level of skin) or other skin parameter.

US 2003/026110 A1 discloses an illumination system previously determined for an illumination direction and an illumination position to an object to be observed which is disposed to an imaging head, while a lens is disposed to an apparatus body, so that the number of parts for the imaging head mounted to an apparatus body can be reduced, precision fabrication such as alignment of lens optical axis is no longer necessary upon manufacture of the imaging head and optimum illumination can be illuminated in accordance with the magnification ratio or the object to be observed by merely exchanging the imaging head, illumination light optimal to the magnification ratio or object to be observed can be obtained with no provision of various kinds of expositive lens units.

US 2001/050765 A1 discloses a fingerprint optical input apparatus comprising a contact image sensor for viewing a moving finger and providing a high contrast image. A narrow strip of the fingerprint touching a transparent platen is illuminated by sheet of collimated light normal to or at an oblique angle to the surface. The fingerprint image is viewed at an oblique angle by partially scattered light or by frustrated total internal reflection. Various embodiments of the platen provide a compact design by using TIR or mirror reflections of the fingerprint image.

SUMMARY OF THE INVENTION

It is an object of the present invention to provide an accessory device and an imaging device, which allow for easy and efficient capturing of a skin image of a subject's skin, which can be used to determine a subject's skin parameter, such as gloss and/or hydration.

It is a further object of the present invention to provide a method, which allows for easy and efficient determination of a subject's skin parameter, such as gloss and/or hydration.

In a first aspect of the present invention an accessory device for an image-capturing device for capturing a skin image of a subject's skin is presented comprising:
  a tubular member having a first opening at its first end configured to surround a light source and an image sensor included in the image-capturing device and a second opening at its second end configured to surround a skin portion;
  two mirrors arranged within the tubular member at its second end, wherein a first mirror is arranged to reflect light emitted by the light source towards the skin portion and a second mirror is arranged to reflect light reflected from the skin portion towards the image sensor.

In a further aspect of the present invention an imaging device comprising:
  an image-capturing device including a light source for emitting light and an image sensor for receiving light and generating an image, and
  an accessory device as disclosed herein.

In a further aspect of the present invention a method for determining a subject's skin gloss is presented comprising:
  obtaining an image of a skin portion of the subject's skin including specular reflection in response to light emitted onto said skin portion,
  determining the amount of white pixels in the obtained image using a threshold for the pixel value,
  determining a skin parameter based on the amount of white pixels in the obtained image.

In yet further aspects of the present invention, there is provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed image-capturing device, method, processor, computer program and medium have similar and/or identical preferred embodiments as the claimed system, in particular as defined in the dependent claims and as disclosed herein.

The present invention is based on the idea to enable measurement of a desired skin parameter, such as gloss and hydration, by making use of the resources of a person's user device, such as a user's smartphone or smart watch (representing the image-capturing device in an embodiment), together with an add-on tool, i.e. an accessory device, preferably comprising only cheap components, making skin parameter measurement accessible for most consumers. As the data (i.e. a skin image) is acquired by the user device, the method to determine a skin parameter may e.g. be seamlessly integrated in a skin care coaching application provided on the user device.

In an embodiment of the accessory device, the mirrors are provided with one or more markers that are detectable in images taken by the image sensor. This enables easy detection of an image portion used for the evaluation and determination of a skin parameter. The markers are preferably configured such that they are easily detectable with image processing means, e.g. they may be configured in color, size and/or texture such that they can be easily distinguished from skin.

The accessory device may further comprise a mounting mechanism to mount the accessory device to the image-capturing device. For instance, a clamping mechanism may be provided for clamping or otherwise fixing (preferably in an easily attachable and detachable manner) the accessory device to the image-capturing device, e.g. a smartphone.

In another embodiment the accessory device further comprises a hydration sensor for detecting skin hydration, said hydration sensor being arranged at or within the tubular member at its second end to contact the skin portion when the second end of the accessory device is pressed against the skin. This provides additional functionality for the imaging device.

Said hydration sensor preferably comprises a base, an electrode mounted on the base and a guidance mechanism for controlling the electrode pressure on the skin. This represents a simple and space saving embodiment.

The accessory device may further comprise an audio interface for input of an input audio signal, in particular from the image-capturing device, provided to the electrode and for output of an output audio signal captured by the electrode in response to the input audio signal, in particular to the image-capturing device. The input audio signal may thus be transferred via part of the electrode (connected e.g. to the headphone part of an audio port of the image-capturing device) to the skin, and the other part of the electrode (connected e.g. to the microphone part of the audio port of the image-capturing device) receives the output audio signal. The ratio between the input audio signal and the output audio signal is a measure for skin capacitance and/or conductance (depending on the frequency or frequencies of the signal), which relates to skin hydration. Further, the hydration measure may be modified by taking into account the ambient parameters like humidity, weather, etc.

The disclosed imaging device comprises an image capturing device including a light source for emitting light and an image sensor for receiving light and generating an image. Further, the imaging device comprises an accessory device as disclosed herein.

The image-capturing device may generally be any mobile user device having a light source (also called illumination unit) and an image sensor (also called imaging unit). Exemplary (but non-limiting) embodiments include a smartphone, a smart watch, a camera, a tablet, a laptop, etc., which is able to provide the desired functionalities and to which the accessory device may be coupled, preferably such that it can be easily attached to it and detached from it.

The imaging device may further comprise a processing unit for processing the image to determine a skin parameter of the skin portion, from which the light has been received by the image sensor and/or a data interface for transmitting the image to processing device for processing it to determine a skin parameter of said skin portion. Thus, the processing is preferably done within the imaging device, in particular within the image-capturing device (e.g. a processor available as part of the image-capturing device). Alternatively, the captured image data may be sent to an external entity, preferably in a wireless manner (e.g. via Bluetooth™ wireless technology, WiFi, a mobile communications network, etc.), or in a wired manner (e.g. by coupling the imaging device with a computer).

The disclosed method for determining a subject's skin parameter, which can be performed by the processing unit or the processing device, is based on the idea to evaluate the amount of white pixels in the obtained image, which has been found to be a useful measure for determining certain skin parameters, such as skin gloss and/or skin hydration. Hereby, the term "white pixel" shall not be understood in the strict sense of optics as having a pixel that exactly has the color white, but shall be understood more broadly as pixel having a pixel value representing white or almost white. Preferably, in an embodiment a threshold for the pixel value is used for determining the amount of the white pixels in the obtained image, i.e. the threshold is used for interpreting a certain pixel as white pixel or as non-white pixel.

The threshold may include in another embodiment one or more fixed or adaptable thresholds for pixel brightness and/or pixel colors, in particular one or more adaptable thresholds that are set based on average brightness and/or average color information in the image and/or based on the subject and/or type of subject.

In a further embodiment the step of obtaining an image of a skin portion includes obtaining a skin image captured by an imaging device as disclosed herein, and extracting from the obtained skin image an image portion reflected by one of the mirrors of the accessory device for further processing an image to determine the subject's skin parameter. For the extraction, image processing means may be used, for instance by detecting markers provided on the mirrors as explained above.

In another embodiment the skin gloss is determined as a skin parameter based on the amount of white pixels in the obtained image. Hereby, the distribution of specular reflection in an image is interpreted to detect the character of the gloss (e.g. oily vs. clean).

The method may further comprise determining a gloss score indicating the amount and/or character of skin gloss based on two or more parameters selected from the group of parameters comprising the amount of white pixels, the amount of clusters of adjacent white pixels, the average cluster size, and the maximum cluster size, in particular by a weighted combination of all parameters. The weights are hereby determined by a best fit analysis, i.e. the disclosed method may further comprise performing a best fit analysis by determining weights used in a weighted combination of two or more of said parameters to one or more predetermined combinations obtained for a set of different images showing different amounts and/or characters of skin gloss.

In another embodiment a skin gloss map may be determined of the skin area indicating the amount of skin gloss per pixel or per group of pixels. This skin gloss map may then be outputted to the user, e.g. on a display, or an average skin gloss value may be determined for the skin areas for which the skin gloss map is determined.

In still another embodiment the method may further comprise the steps of obtaining an average value of a skin parameter from determinations of said skin parameter for different subjects over a time period, and comparing a currently determined value of the skin parameter determined for the current subject with the average value to classify the currently determined value of the skin parameter. This ensures that the user gets more and/or better information regarding the determined skin parameter supporting a better interpretation and understanding of the actual measurement.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1A:
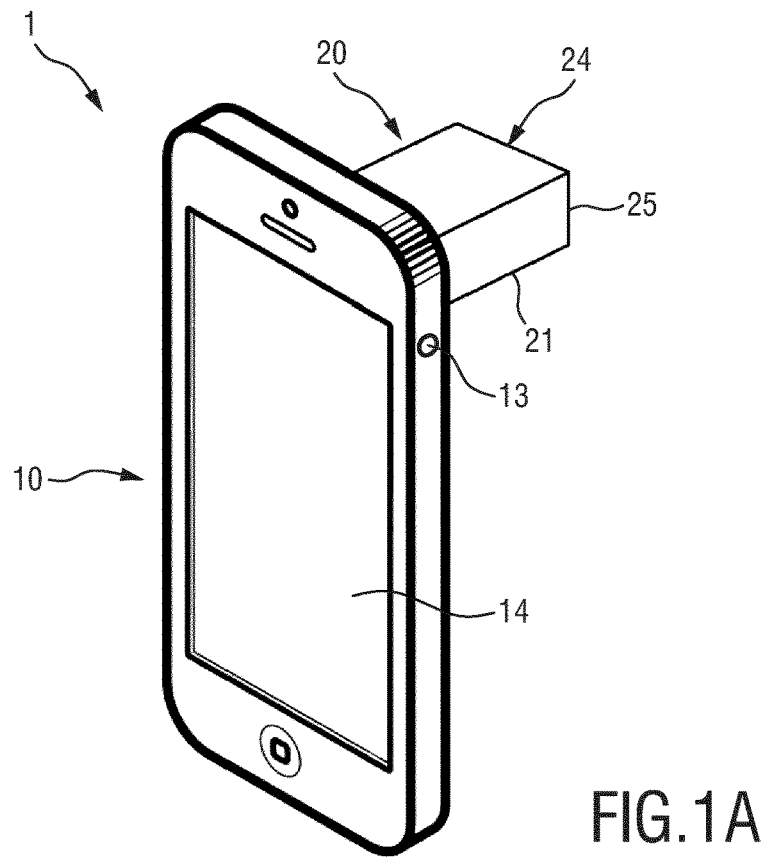
FIGS. 1A and 1B show a front view and a rear view of an exemplary implementation of a first embodiment of an imaging device including an accessory device according to the present invention.
Figure 1B:
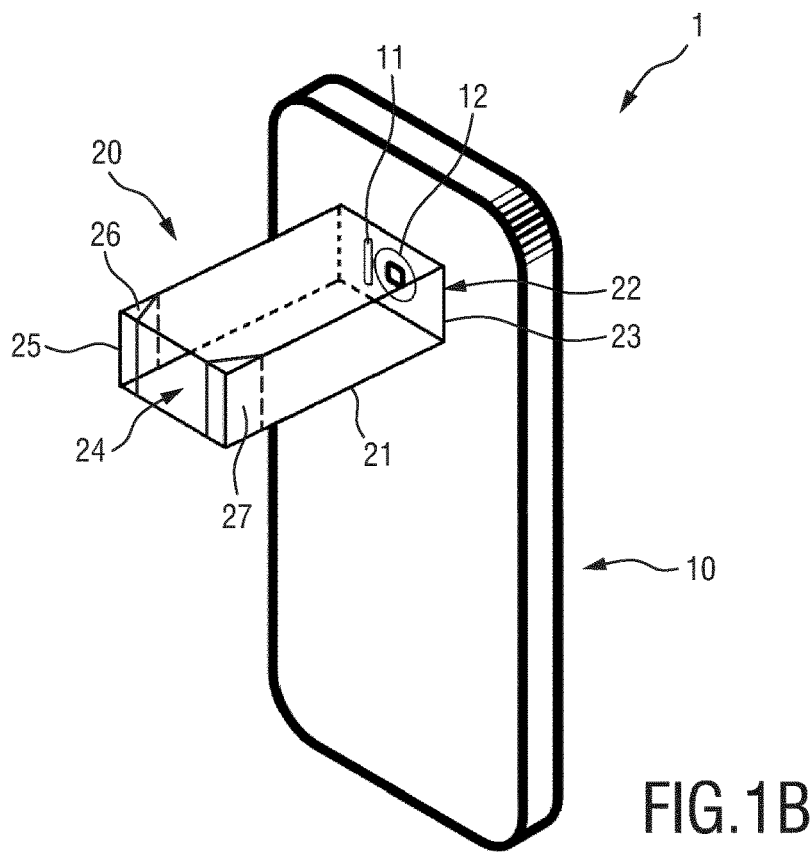
Figure 2:
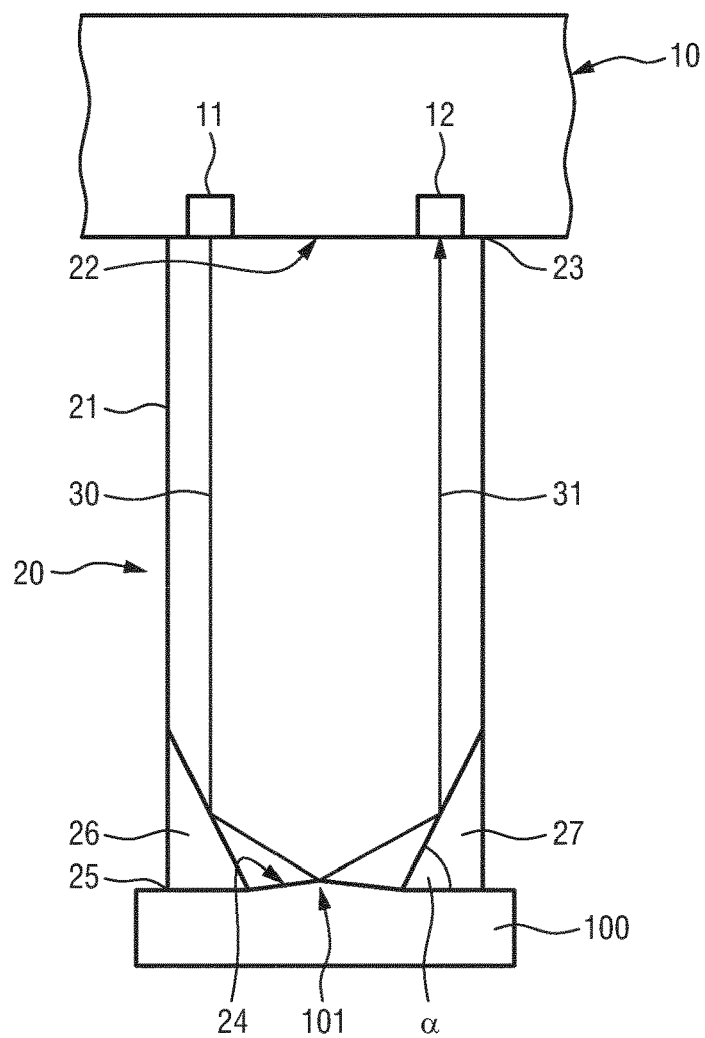
FIG. 2 shows a schematic diagram illustrating the principle of the present invention.

FIG. 1 shows a front view (FIG. 1A) and a rear view (FIG. 1B) of an exemplary implementation of a first embodiment of an imaging device 1 according to the present invention. FIG. 2 shows a schematic diagram illustrating the principle of the present invention.

The imaging device 1 comprises an image-capturing device 10 including a light source 11 for emitting light 30 and an image sensor 12 for receiving light 31 and generating an image. In this exemplary embodiment the image-capturing device 10 is a smartphone that comprises a flash and/or torch light for use as light source 11 and a camera for use as image sensor 12. The image-capturing device 10 may further (optionally) comprise an audio interface 13 and a display 14.

The image-capturing device 10 may comprise further optional elements, such as a control unit for controlling the light source 11 and/or the image sensor 12. The task of the control unit may, however, also be performed by a processor, or the tasks of the light source 11 and/or the image sensor 12 may be predetermined and fixed so that an active control unit may not be required.

The device 1 may further comprise a user interface, e.g. the display 14, keypad, touchscreen, etc., allowing the user to enter information, e.g. to start and stop skin parameter detection, change settings, enter personal information, etc., and enabling output of information, e.g. the detected skin parameter information or user instructions.

The accessory device 20 comprises a tubular member 21 having first opening 22 at its first end 23 configured to surround the light source 11 and the image sensor 12 of the image-capturing device 10 and a second opening 24 at its second end 25 configured to surround a skin portion 101 of a person's skin 100, e.g. a portion of the cheek or forehead of the person's face. Further, the accessory device 20 comprises two mirrors 26, 27 arranged within the tubular member 21 at its second end 25 to reflect light 30 emitted by the light source 11 towards the skin portion 101 and to reflect light 31 reflected from the skin portion 101 towards the image sensor 12.

As shown in FIG. 2, for performing a measurement the accessory device is arranged between the skin portion 101 and the image-capturing device 10. For instance, it can be held by hand and pressed against the skin 100 or it can be mounted to the image-capturing device 10. From the image captured by the image-capturing device 10 a skin parameter can be determined, e.g. by the image-capturing device 10 or an external entity, e.g. a computer to which the image is sent. The method for determining a skin parameter will be explained below in more detail.

In an embodiment the mirrors 26, 27 are arranged at an angle α in the range of 45°-75° (e.g. at about 60°) with respect to the measurement plane, i.e. the plane of the second opening 24 and thus the surface of the skin portion 101 visible for the image sensor 12 through the second opening 24. The mirror 26 reflects the light 30 under a shallow angle (e.g. in the range of 15°-45°) onto the skin. From the other mirror 27 the reflection image is acquired that is used to determine the skin parameter, e.g. to calculate a gloss score.

Figure 3:
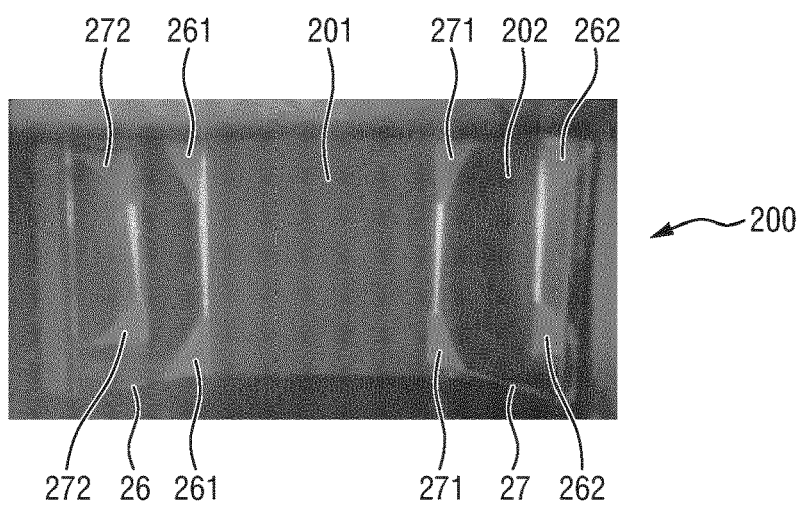
FIG. 3 shows a diagram illustrating a view through the second opening of the accessory device according to the present invention.

FIG. 3 shows a diagram illustrating a view 200 through the second opening 24 of the accessory device 20. The view 200 shows a direct skin view 201 of the skin portion 101, the first (illuminating) mirror 26 and the second (reflecting) mirror 27 showing a mirror image 202 of the skin portion 101. Further, marker 261 and 271 as provided on the mirrors 26, 27, in this embodiment as small triangles shown in two corners of each mirror 26, 27, as well as reflection 262, 272 of the markers 261, 271 in the respective other mirror are shown in the view 200. Of course, other kinds, positions and/or numbers of markers can be used that ensure that they can be recognized and used for identifying the different portions of the view 200.

Hence, according to the present invention one mirror is used to illuminate the skin under a shallow angle, the other mirror is used to capture the image of the specular reflected light (i.e. light having an angle of incidence identical to the angle of reflection according to Snellius' law). At a shallow angle much more light is reflected from the surface of the skin and the oily substance on the skin. Light illuminating the skin under e.g. an angle of 90° is largely absorbed. When illuminating the skin under shallow angles, in order to see the specular reflected light, the same (but mirrored) angle is observed and evaluated.

Figure 4:
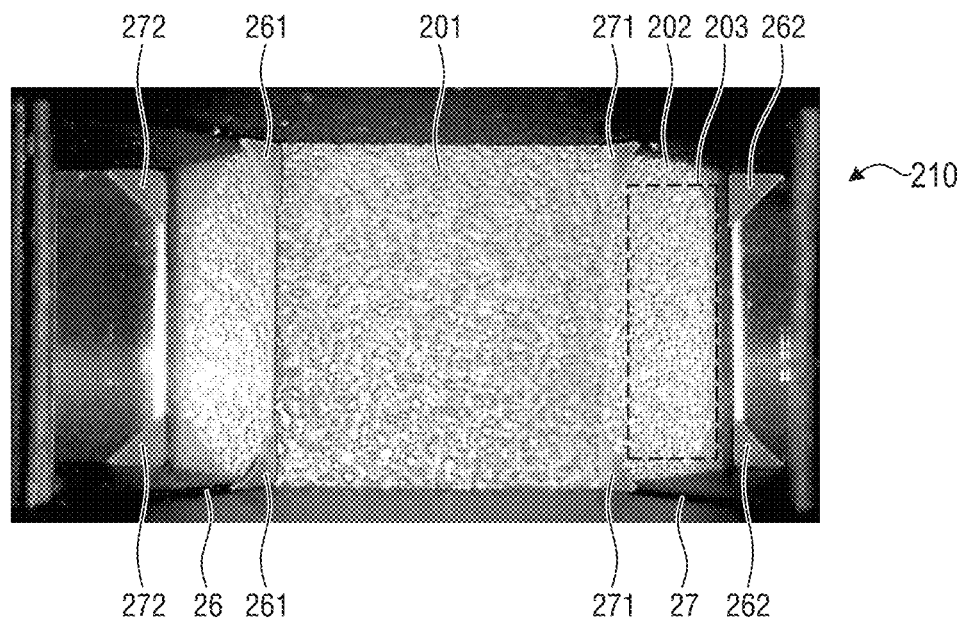
FIG. 4 shows an exemplary image acquired by an imaging device according to the present invention.

This is illustrated in FIG. 4 showing an exemplary image 210 (corresponding to the view 200) acquired by the imaging device according to the present invention, i.e. of an image 210 as seen through the second opening 24 of the accessory device 20. In the mirror image 202 a measurement area 203 may be defined which is used as the image of the skin portion for evaluation and determination of the skin parameter.

While taking the image, focal distance, shutter time, color correction, and/or torchlight/flashlight illumination settings may be all controlled to create, in combination with the exclusion of external light sources, reproducible images.

Figure 5:
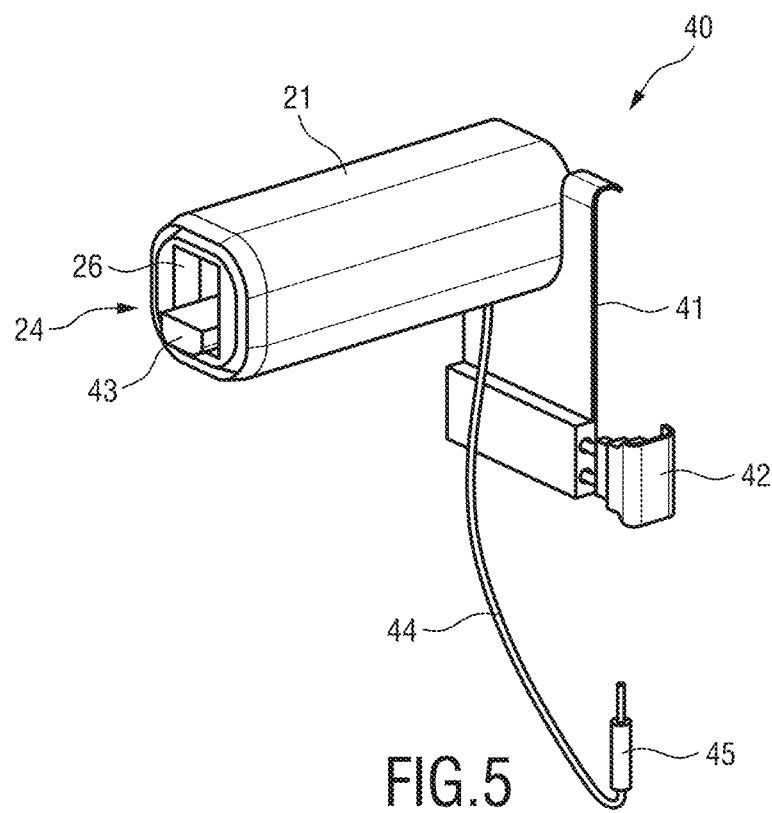
FIG. 5 shows a perspective view of an exemplary implementation of a second embodiment of an accessory device according to the present invention.

FIG. 5 shows a perspective view of an exemplary implementation of a second embodiment of an accessory device 40 according to the present invention. This embodiment of the accessory device 40 comprises a base 41 onto which the tubular member 21 is mounted and a clamping mechanism 42 to secure and position the accessory device 40 to the image-capturing device 10, e.g. to a smartphone.

In this embodiment the accessory device 40 comprises an optional hydration sensor 43 that is connected to an audio cable 44 with a jack-plug 45 that can be inserted into the audio socket of the image-capturing device 10, e.g. of a smartphone. The accessory device 40 clicks from one end on the image-capturing device 10 covering the light source 11 and the image sensor 12 of the image-capturing device 10, e.g. the camera and flash/torchlight of the smartphone as shown in FIG. 1.

For imaging the user may press the other end of the tubular member 21, containing the two mirrors 26, 27 onto his/her skin. When the tubular member is in position, the software will make a picture with controlled flash or controlled torchlight and analyze the picture, e.g. the image in the measurement area 203 as shown in the mirror 27 (see FIG. 4).

Figure 6:
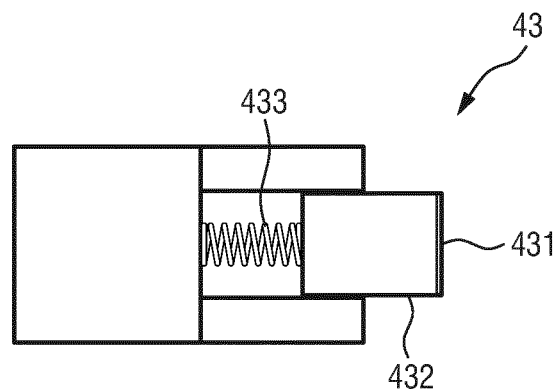
FIG. 6 shows an embodiment of a hydration sensor as optionally used in an embodiment of an accessory device according to the present invention.

As mentioned, it is also possible to integrate a hydration sensor 43 into the tubular member 21 for gloss measurement. An embodiment of a hydration sensor 43 is shown in FIG. 6. It comprises an electrode 431 mounted on a base 432 that has a linear guidance and spring mechanism 433 for controlling the electrode pressure on the skin during measurement. Via an audio interface 13 (see FIG. 1) of the image-capturing device 10, e.g. an audio jack headphone output, an alternating signal, for instance with a frequency of 16 kHz, is transmitted and the response is acquired via the audio interface, e.g. a microphone input of the same audio jack. Given a defined output signal, the acquired input signal is a measure for skin impedance, which is mainly determined by skin hydration.

Figure 7:
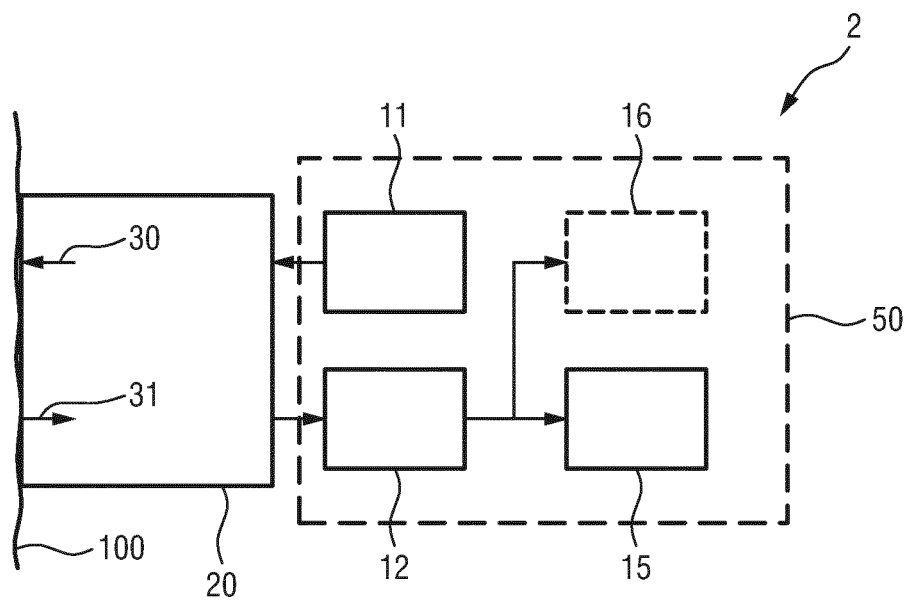
FIG. 7 shows a schematic diagram of a second embodiment of an imaging device according to the present invention.

FIG. 7 shows a schematic diagram of a second embodiment of an imaging device according to the present invention. In addition to the elements of the imaging device 1 shown in FIG. 1, the imaging device 2, in particular the image-capturing device 50, comprises a processing unit 15 for processing the image to determine a skin parameter of the skin portion, from which the light has been received by the image sensor 12 and/or a data interface 16 for transmitting the image to an external processing device (not shown), e.g. a computer, a server, the cloud, etc., for processing it to determine a skin parameter of said skin portion. The processing unit 15 may e.g. be the main processor of the image-capturing device 50. The data interface 16 may be a an interface for outputting the image in wireless or wired manner.

Figure 8:
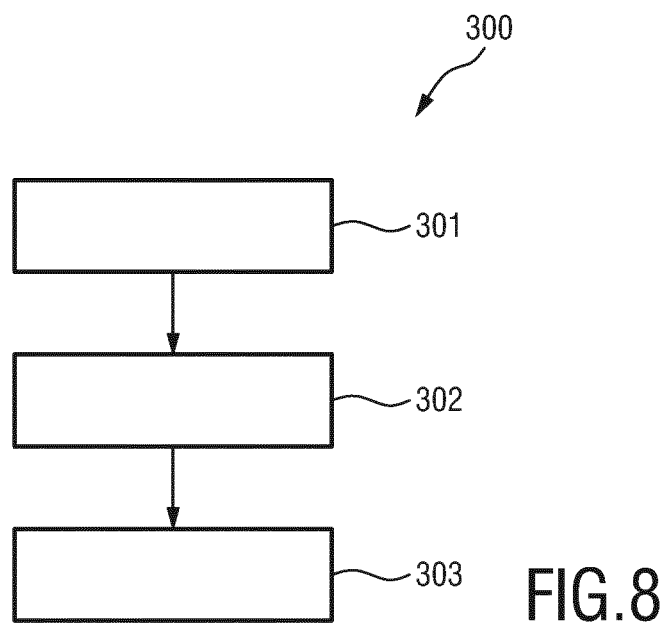
FIG. 8 shows a flow chart of a first embodiment of a method for skin parameter detection according to the present invention.

FIG. 8 shows a flow chart of an embodiment of a method 300 for skin parameter detection according to the present invention. In a first step 301 an image of a skin portion 101 of the subject's skin 100 including specular reflection in response to light emitted onto said skin portion 101 is obtained. In a second step 302 the amount of white pixels in the obtained image is determined using a threshold for the pixel value. In a third step 303 a skin parameter is determined based on the amount of white pixels in the obtained image.

In an embodiment the amount and distribution of the white pixels in the image is determined. The distribution of white pixels may include one or more of the parameters "amount of clusters of white pixels", "average cluster size", "maximum cluster size" and "average intensity of the white pixels" in the image. The amount of white pixels in the image, together with the parameters mentioned before, may then be used in a transfer-function to calculate a gloss score. This score can then be used to give feedback and guidance to the consumer.

In the following more details of an embodiment of the method according to the present invention are discussed. From the image taken by the imaging device, by using the markers (as shown in FIG. 3), the mirror image of one of the two mirrors is isolated, e.g. by an algorithm. This isolated mirror image shows the skin surface, including the specular reflection. A fixed threshold is set for defining white pixels, meaning a lower threshold for the R, G and B values of the pixels.

When counting the amount of white pixels in the mirror image, this may be used as a measure for the specular reflection e.g. skin gloss. Because the external light sources are excluded due to the use of the tubular member 21, a fixed threshold for white pixel definition can be used (no compensation for other factors needed) and the amount of white pixels can be compared between images and used for a conclusion on more or less gloss.

The amount of white pixels in the image is normalized with respect to the total amount of pixels in the isolated mirror image, to compensate for minor variation in hardware. Counting the amount of pixels in an image that comply with a certain color definition is a standard function, e.g. in open source computer vision software.

One benefit of this method is its simplicity. Only low calculating power is needed, making it suitable for multiple low cost hardware platforms. This method makes particular sense in combination with image acquisition that creates reproducible images, as described in the above method for image acquisition.

In the above described embodiment a fixed threshold is set. In another embodiment the threshold may be set based on average color information in the image. The advantage of this is that people with very white skin would not per definition have a higher white pixel count than people with very dark skin. However, this may require additional image analysis steps. A way to circumvent that is to have a user indicate his/her skin tone (for instance using the Fitzpatrick color scale), and based on that indication a skin color specific threshold may be set.

Current skin gloss measurements give an absolute value for specular reflection. For measurement devices used by a specialist (skin expert, beautician), where the specialist does the interpretation, taking into account other physiologic aspects of the person (amongst others skin texture, age, shape of the measured area), this is sufficient. However, for a gloss measurement device used on a regular basis by a consumer (e.g. laymen) an absolute value without interpretation is of less meaning. In the following another embodiment of the method is described that solves disadvantages of an absolute gloss measurement: it uses the distribution of the gloss in the image to assess if the gloss measured is "oily shine" or "hygienic", giving a higher value to oily gloss and a lower value to hygienic gloss. Furthermore it concludes on an "average" or "regular" parameter value for a specific person and compares a new measured value to that, enabling an action on the size of the difference instead of on the absolute value of the parameter.

Knowing when a skin is glossy or not may already be relevant information for a user, or may be used as input for giving a user skin care coaching. However characterizing gloss into desired gloss (healthy clean radiation) or undesired gloss (oily, sweaty skin) has additional benefit. Besides having absolute levels of gloss, the distribution of gloss in the acquired image also contains information about the character of the gloss. Based on expert assessment it is believed that "oily" gloss has a more granular/droplet like distribution and "clean" gloss has a more diffuse/egg gloss appearance.

Parameters used in this embodiment for characterizing gloss may include one or more of pixel count (amount of white pixels in the image), blob count (blob=cluster of more than 4 white pixels), average blob size (amount of adherent white pixels), and maximum blob size.

In this embodiment, a combined gloss score is defined by a transfer function of white pixel count, blob count, average blob size and maximum blob size:

$$GC = C0 + C1*Pixel\_count + C2*Blob\_count + C3*Av\_blob\_size + C4*Max\_blob\_size$$

in which C0 . . . C4 are constants.

A best parameter fit of the transfer function is created by finding the best fit of the output of the transfer function, e.g. with an expert panel assessment of a defined set of skin gloss images. The defined set comprises images of a group of people having varying skin types, wherein images are taken of a defined skin location, for instance the forehead and images are taken of several "states" of the skin, for instance a "natural" state, a state directly after cleansing and a state in which the skin is given an oily appearance (for instance by distribution of a cosmetic oil). The images of the various skin states are then ranked by an expert panel. After that, the GC function is optimized to a best fit with the expert panel assessment.

The method disclosed herein can be used the parameter of skin gloss, but is not limited to that. Many other skin parameters can be determined, for instance skin roughness, elasticity, pigmentation, vary with changing location and measurement circumstances, like environmental conditions, but also pressure and angle of placement during use. For instance, for determining roughness/texture of the skin, edge detection can be used to discriminate deepened edges (shadows) from higher structure (illuminated). The distribution and size of shadow and light areas is a measure for roughness. Pigmentation (areas with more melanin compared to surrounding skin) can be identified by color thresholding: a pigment spot has a color within certain bandwidth (LAB and/or RGB, brown-reddish). The surrounding skin is lighter.

When measuring a skin parameter on a specific location on human skin, within a series of repeated measures within a short span of time (e.g. minutes), assuming the skin itself is not changing, still quite some variation between the measurements within a series can be found. However, when the average value and the measurement variation for a location is known, for each newly measured value the probability can be assessed if the value is statistically different from the average or not. Depending on the action intended when finding a value deviating from the average, the needed certainty of making the right call on that can be defined.

The interpretation of the value is independent of the absolute value of the skin parameter. Because of that, it can be used for every single person, regardless of the absolute average value of the skin parameter.

As skin changes over time, for instance due to aging and change of seasons, a person's average parameter (e.g. gloss) will also vary over time. It is known that for most people gloss values in winter are typically lower than gloss values in summertime. For that, according to an embodiment of the method, besides an absolute average based on all measurement values of a person, also a moving average, containing a limited set of values, can be used.

Figure 9:
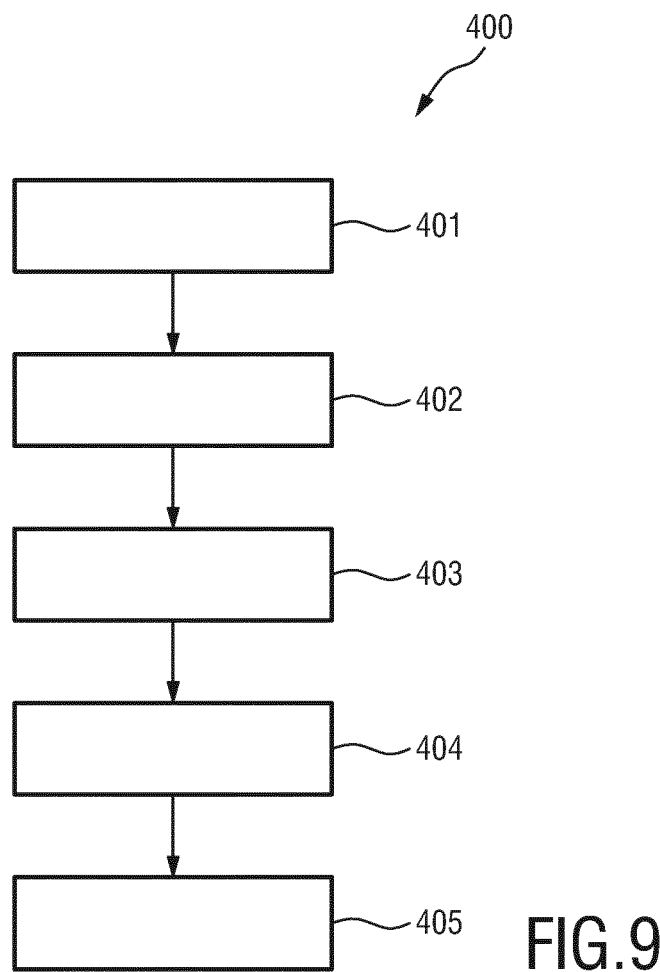
FIG. 9 shows a flow chart of a second embodiment of a method for skin parameter detection according to the present invention.

In such an embodiment, the method may comprise the following steps as illustrated in FIG. 9 showing a flowchart of said method 400:

Step 401: Acquire sufficient measurement values of a specific area, within a relative short period of time (for instance a week, limited skin changes) to calculate average and variation (for instance standard deviation).

Step 402: Define the amount of values to include in the moving average (minimum 2 values, max all values)

Step 403: Define the bandwidth around the moving average, based on variation found and certainty needed, for which a value is considered different (higher or lower) from average when being outside that bandwidth.

Step 404: Based on a new value found: assess if it is different from the average.

Step 405: Use the last value for recalculating the moving average.

This embodiment of the method may be further refined. For instance, when a variation is found (i.e. a variation bandwidth around average) that is small enough (i.e. below a threshold), the classification of a found value with respect to the average can be refined. One possible classification may be: lower, similar, or higher than the average. A finer classification may be: between xx and yy % lower or between xx and yy % higher than the average.

As alternative to the use of a moving average, the method of Kalman filtering (which is generally well known in signal processing) can be used. In this embodiment, also an assessment may be made of the measurement variation a person will encounter. Knowing the variation, the parameter settings for the Kalman filtering can be defined.

The imaging device according to the present invention may be a mobile user device, for instance a smartphone, camera, laptop, smart watch or tablet, which is available to many users for everyday use and which is adapted for the desired purpose of detecting a skin parameter, e.g. by use of a software application ('app') that makes use of existing hardware components and evaluates data that are obtained by existing hardware components. Alternatively, the imaging device may also be a dedicated device made particularly for the purpose of skin parameter detection (and optionally other purposes).

Known skin measurement devices meant for consumers may include hydration measurement, but do not contain a relevant and reliable gloss- or oil measurement at an affordable price. With that, it is difficult to give accurate personalized skin care advice for maintaining a hygienic appearance combined with a healthy skin hydration level. By use of the present invention, skin parameters such as skin gloss and skin hydration can be reliably determined making e.g. use of a person's own user device, such as a smartphone, in combination with an add-on tool. Hence, a proper skin care advice can be given to the user at a low price.

The present invention can be applied in any personal care proposition where having knowledge on a desired skin parameter, e.g. skin gloss and hydration, is relevant for better guidance of the user on his or her skin care routine, or where info on a particular skin parameter, e.g. skin gloss and hydration, is relevant to change the settings of a personal care device.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An image-capturing device for capturing a skin image of a subject's skin, wherein the image-capturing device has a light source and a single image sensor configured to detect light emitted by the light source, both the light source and the single image sensor adjacently positioned on or within a surface of the image-capturing device, and further comprising:
   an accessory device, said accessory device comprising:
     a tubular member comprising a first opening at its first end configured to surround, when the accessory device is detachably mounted to the image-capturing device, the light source and the image sensor included in the image-capturing device, the tubular member further comprising a second opening at its second end configured to surround a skin portion; and
     first and second mirrors arranged within the second end of the tubular member, wherein the first mirror is arranged to reflect, when the accessory device is detachably mounted to the image-capturing device, light emitted by the light source towards the skin portion and the second mirror is arranged to reflect, when the accessory device is detachably mounted to the image-capturing device, light reflected from the skin portion towards the image sensor, wherein each of the first and second mirrors is provided with one or more markers that are detectable in images of the subject's skin taken by the image sensor, and wherein the one or more markers of the first and second mirrors are the same or different;
   a processor configured to process the image to determine a skin parameter of the skin portion from which the light has been received by the image sensor, wherein the skin parameter comprises skin gloss and the processor is configured to determine a gloss score indicating an amount or a character of skin gloss based on determination of: (i) an amount of white pixels in the skin portion; (ii) a number of clusters of white pixels in the skin portion, wherein a cluster is 4 or more adjacent white pixels; (iii) an average size of the number of clusters of white portions in the skin portion, where a size of a cluster is a number of white pixels in the cluster; and (iv) a largest cluster, by size of the cluster, in the skin portion, and further wherein the gloss score is determined using the following equation:

$$C0+C1*\text{pixel count}+C2*\text{cluster count}+C3*\text{average cluster size}+C4*\text{max cluster size}$$

where pixel count is the determination of the amount of white pixels in the skin portion, cluster count is the determination of the number of clusters of white pixels in the skin portion, average cluster size is the determination of the average size of the number of clusters of white portions in the skin portion, max cluster size is the determination of the largest cluster in the skin portion, and C0, C1, C2, C3, and C4 are constants.

2. The image-capturing device as claimed in claim 1, further comprising a mounting mechanism to mount the accessory device to the image-capturing device.

3. The image-capturing device as claimed in claim 1, further comprising a hydration sensor for detecting skin hydration, said hydration sensor being arranged at or within the tubular member at its second end to contact the skin portion when the second end of the accessory device is pressed against the skin.

4. The image-capturing device as claimed in claim 3, wherein said hydration sensor comprises a base, an electrode mounted on the base and a guidance mechanism for controlling an electrode pressure on the skin.

5. The image-capturing device as claimed in claim 4, further comprising an audio interface for input of an input audio signal provided to the electrode and for output of an output audio signal captured by the electrode in response to the input audio signal.

6. The image-capturing device as claimed in claim 1, wherein the first mirror is configured to reflect light from the light source to illuminate the skin portion at a first angle and the second mirror is configured to reflect, towards the image sensor, light having an angle of incidence that is equal to the first angle.

7. The image-capturing device as claimed in claim 1, further comprising:
   an interface for transmitting the image to the processor for processing the image to determine a skin parameter of said skin portion.

8. The imaging-capturing device as claimed in claim 7, wherein the interface comprises a wired or wireless communication interface.

* * * * *